(12) United States Patent
Meftah et al.

(10) Patent No.: US 9,649,043 B2
(45) Date of Patent: May 16, 2017

(54) SLEEP POSITION DETECTION

(75) Inventors: Mohammed Meftah, Eindhoven (NL); Andreas Brauers, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 2071 days.

(21) Appl. No.: 12/747,176

(22) PCT Filed: Dec. 9, 2008

(86) PCT No.: PCT/IB2008/055164
§ 371 (c)(1),
(2), (4) Date: Jun. 10, 2010

(87) PCT Pub. No.: WO2009/074995
PCT Pub. Date: Jun. 18, 2009

(65) Prior Publication Data
US 2010/0262026 A1    Oct. 14, 2010

(30) Foreign Application Priority Data
Dec. 12, 2007    (EP) ..................... 07122981

(51) Int. Cl.
*A61B 5/04*    (2006.01)
*A61B 5/0408*    (2006.01)
(Continued)

(52) U.S. Cl.
CPC ...... *A61B 5/04085* (2013.01); *A61B 5/04011* (2013.01); *A61B 5/1114* (2013.01); *A61B 5/1116* (2013.01); *A61B 5/4806* (2013.01); *A61B 5/6887* (2013.01); *A61B 5/6892* (2013.01); *A61B 2562/046* (2013.01)

(58) Field of Classification Search
None
See application file for complete search history.

(56) References Cited

U.S. PATENT DOCUMENTS 4,101,768 A    7/1978    Lill
5,476,501 A *  12/1995   Stewart et al. ............... 607/127
(Continued)

FOREIGN PATENT DOCUMENTS

JP    200457507 A    2/2004
WO    9919715 A1    4/1999
(Continued)

OTHER PUBLICATIONS

Shinar et al: "Obstructive Sleep Apnea Detection Based on Electrocardiogram Analysis"; Computers in Cardiology 2000, vol. 27, pp. 757-760.
(Continued)

*Primary Examiner* — Brian T Gedeon
*Assistant Examiner* — Ankit D Tejani

(57) ABSTRACT

A method of determining body position uses ECG sensors at fixed positions, not fixed to the patient. The ECG signals recorded from the sensors are used to detect body position, using the variation of ECG potential over the surface of the body. The results may be processed by measuring artifacts related to the angle between the sensors and the heart, in particular the polarity of the QRS complex. The sensors may be fixed on the upper surface of a bed and used to measure sleep position.

16 Claims, 3 Drawing Sheets

(51) Int. Cl.
*A61B 5/11* (2006.01)
*A61B 5/00* (2006.01)

(56) References Cited

U.S. PATENT DOCUMENTS

| | | |
|---|---|---|
| 5,865,760 A | 2/1999 | Lidman et al. |
| 2003/0083586 A1* | 5/2003 | Ferek-Petric ................. 600/512 |
| 2004/0111045 A1* | 6/2004 | Sullivan et al. .............. 600/595 |
| 2006/0235315 A1 | 10/2006 | Akselrod et al. |
| 2007/0255152 A1* | 11/2007 | Park et al. .................... 600/513 |
| 2007/0276270 A1* | 11/2007 | Tran ............................. 600/508 |
| 2008/0208063 A1* | 8/2008 | Brauers et al. ............... 600/481 |
| 2010/0041975 A1* | 2/2010 | Chen et al. ................... 600/393 |

FOREIGN PATENT DOCUMENTS

| | | |
|---|---|---|
| WO | 2005096946 A1 | 10/2005 |
| WO | 2006031025 A1 | 3/2006 |
| WO | 2006131855 A2 | 12/2006 |
| WO | 2007060609 A2 | 5/2007 |

OTHER PUBLICATIONS

Shinar et al: "Detection of Different Recumbent Body Positions From the Electrocardiogram"; Medical & Biological Engineering & Computing, 2003, vol. 41, pp. 206-210.
Garcia et al: "ECG-Based Detection of Body Position Changes in Ischemia Monitoring"; IEEE Transactions on Biomedical Engineering, vol. 50, No. 6, Jun. 2003.

* cited by examiner

SLEEP POSITION DETECTION

FIELD OF THE INVENTION

The invention relates to a method and apparatus for measuring body position.

BACKGROUND OF THE INVENTION

There has been an increasing interest in the monitoring of various vital body signs for a number of reasons.

There is an interest in monitoring the position of the human body for a number of reasons.

A particular issue is sleep disorder. Sleep disorder is a very widespread phenomenon. About 40% of American adults suffer from some kind of sleep disorder while about 70 million Americans are chronically sleep deprived. Accordingly, measurement of sleeping quality and sleep disturbances is required. As well as vital parameters such as heart rate, respiration rate and body temperature, body position is an important parameter in such measurements.

The measurement of body position can also be important to detect changes in body position where this is needed for medical reasons, for example for people who are at risk of developing a decubitus sore or ulcer.

It is further beneficial if the measurement of body position should be unobtrusive. Sensors should in particular be unobtrusive, unrestrictive and comfortable for the user.

A particular system for detecting changes in body posture using an electrocardiogram (ECG) is described in U.S. Pat. No. 5,865,760. The ECG is analyzed to detect artefacts caused by changes in body posture.

SUMMARY OF THE INVENTION

According to the invention there is provided sleep position detection apparatus according to claim 1.

The inventors have realized that by measuring the ECG traces with a plurality of sensors arranged in a position not fixed with respect to the body but fixed with respect to a support the sensors can use the variation in the body surface potential caused by the electrical activity of the heart at different positions on the body to measure the body position. In contrast, prior art sensors attached to the body measure the body surface potential at constant locations on the body. The variation of ECG signal over the body means that the use of sensors fixed with respect to the support results in much greater differences in ECG traces as the body moves than using sensors attached to the body.

Preferably, the sensors are capacitive sensors which do not need to be in direct contact with the skin. This enables conventional nightwear to be worn.

The sensors may be arranged in an array across the body support. This allows measurements to be taken with the body in different positions above different sensors in the array.

In another aspect, there is provided a method of measuring body position according to claim 9.

BRIEF DESCRIPTION OF THE DRAWINGS

For a better understanding of the invention, embodiments will now be described, purely by way of example, with reference to the accompanying drawings, in which.

The Figs. are schematic and not to scale.

DETAILED DESCRIPTION OF THE EMBODIMENTS

Figure 1:
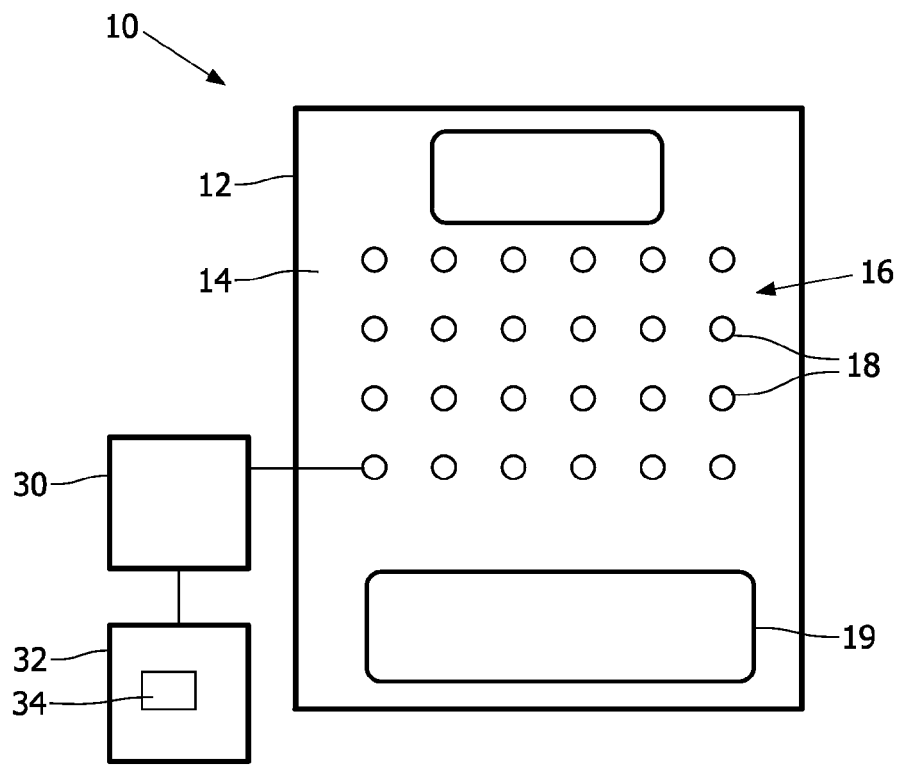
FIG. 1 shows a first embodiment of the invention.

Referring to FIG. 1, apparatus according to an embodiment of the invention includes a bed 10 with a mattress acting as a body support 121 having an upper sleeping surface 14, which acts in use as a body support.

A plurality of sensors 18 are arranged as an array 16 over the upper sleeping surface 14. The sensors are connected to processor 30 which in turn is connected to memory 32 including code 34 for carrying out the method as set out below.

The sensors 18 are capacitive sensors of the type described in WO 2007/060609 (Philips). Such sensors are able to detect electrocardiogram signals without being in physical contact with the patient, leading to the distinct advantage that the patient can wear normal clothing, pyjamas, in bed.

Note that a capacitively coupled return path may be used, for example capacitive plate 19 at the foot of the bed. This is used to reject common mode interference, especially at mains electricity frequencies (50 Hz/60 Hz).

Figure 2:
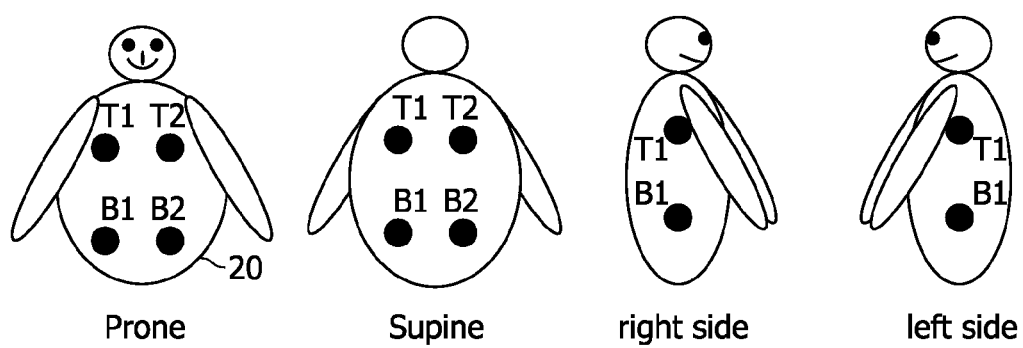
FIG. 2 shows a plurality of body positions.

FIG. 2 illustrates four sleeping positions of a patient 20, lying over four sensors 18. In FIG. 2, these sensors are labeled T1, T2, B1 and B2. It will be appreciated that these represent the four sensors on the upper surface over which a patient happens to be lying. The four positions are prone (lying on the front), supine (lying on the back), right side (lying facing the right side) and left side (lying facing the left side). Note that in the latter two positions the patient is only lying on two sensors, T1 and B1, in view of the smaller area of contact with the upper sleeping surface in these positions.

Figure 3:
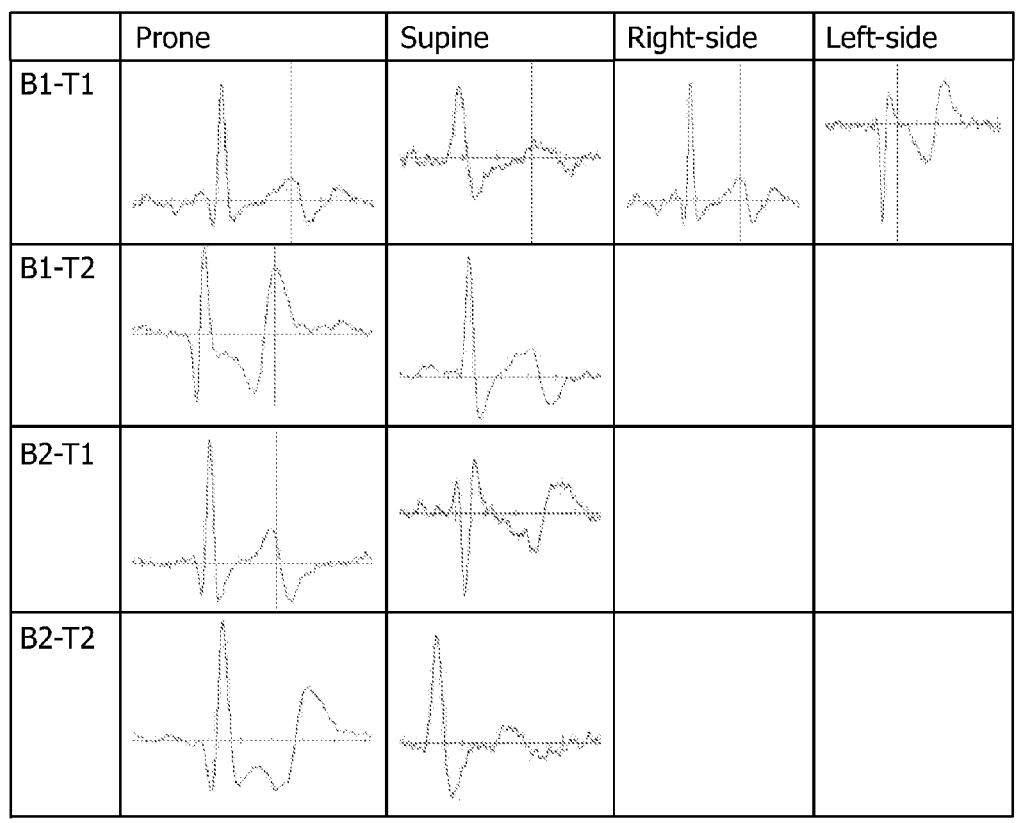
FIG. 3 shows a results measured in the plurality of body positions.

The different body positions lead to clearly different waveforms as shown in FIG. 3. For the two positions in which only the T1 and B1 sensors are covered by the patient, only the ECG measurement between these two sensors is recorded; for the other two positions, four measurements are recorded.

The body surface potential mapping of the electrical activity of the heart is the mapping of potential over the body. The sensors fixed at known locations measure this potential and so give a measure of the body orientation. In contrast, sensors attached to the patient always pick up the body surface potential from the same point on the body. This would give much smaller changes with different body position.

In particular, note that the polarity of the QRS complex gives significant data. In the case that this is positive (see the right side data measured between sensors T1 and B1), this indicates that the electrical axis of the heart is parallel to the line of sensors T1 to B1. In contrast, if the polarity is negative (see the left side data measured between sensors T1 and B1) this indicates that the electrical axis of the heart is antiparallel to the line of sensors T1 to B1.

If the polarity is zero, or if the positive branch of the QRS complex is roughly the size of the negative branch of the QRS complex (see for example the measurement prone B1-T2), then the electrical axis of the heart is roughly perpendicular to the line of sensors (here B1 to T2).

In order to automatically determine the position, the effects of variation in the measured waveform due to interpersonal variation or changes in the health status of the person must be taken into account.

In the embodiment, two different approaches are taken to determining body position. Both of these are used in tandem to determine the position.

Firstly, calibration measurements can be obtained by a calibration procedure, which may be done at regular intervals or at user demand. During such a calibration procedure the user is asked to lie in the four different positions, and the measured signals are recorded for each position as calibration signals.

Then, in use, the measured signals are analyzed for similarity to the calibration signals and the closest match used to determine body position.

The alternative approach is to use the identification of the polarity of the QRS complex from at least one and preferably more pairs of sensors. This can then be used to determine the angle of the electrical axis of the heart depending on this polarity, and hence obtain a measure of the user's position.

In the embodiment described, both of these approaches are used by the processor to obtain an estimate of the sleeping position. However, in alternative embodiments, only one or the other might be used.

The sleep position can be determined without the need for additional electronics, mechanics and alike, since it is being extracted from the ECG signal. Moreover, the comfort for the patient is not impaired by additional electrodes attached to the patient.

Note that the use of more than two sensors allows for the apparatus to measure body position even if the body is not located over a particular pair of sensors. In embodiments, information regarding which sensors are able to detect ECG measurements may be combined with the orientation information to determine body position.

Figure 4:
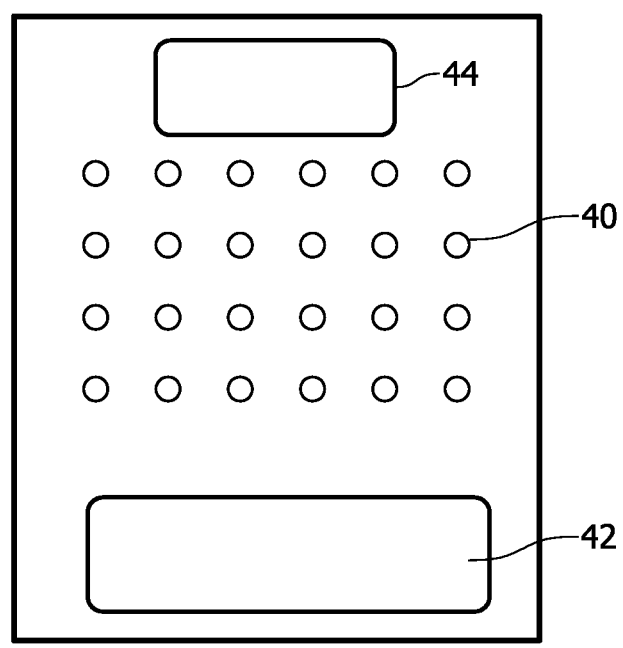
FIG. 4 shows an alternative embodiment of the invention.

In an alternative embodiment, the sensors used are electrically conductive electrodes integrated in a bed sheet as a conductive textile electrode array 40 (FIG. 4). In this case, a foot region 42 of conductive textile serves as a ground plate meant for the reduction of common-mode interference. Alternatively, a conductive pillow 44 may be used as the return path for electricity, or a conventional leg electrode.

In this case, the conductive electrodes need to be in electrical contact with the patient during measurement so that the patient should sleep with a naked trunk, and not in pyjamas.

Further, the sensors need not be arranged in a bed but in another kind of body support, such as a chair for example. Alternatively, the body support could simply be the floor of a room or fixed to the floor of the room and the sensors could be fixed in the room.

The sensors need not be fixed to the body support but simply fixed in position with respect to that support, for example by being fixed to a frame or cover.

Although the above description relates to the human body a similar approach can be used for measuring the body position of animals, especially mammals.

The invention claimed is:

1. Apparatus for measuring body position, comprising:
    at least two biometric sensors arranged in a fixed position with respect to a body support, for measuring at least one electrocardiogram signal from a body, wherein the at least one electrocardiogram signal changes with the body position as a result of variation of electrocardiogram potential over the surface of the body; and
    a processing means arranged to capture the at least one electrocardiogram signal from the biometric sensors, and to determine the body position from the captured at least one electrocardiogram signal using the variation of electrocardiogram potential over the surface of the body;
    wherein the processing means is adapted to determine a polarity of a QRS complex of the at least one electrocardiogram signal to determine an orientation of a heart of the body with respect to a respective pair of the biometric sensors providing the at least one electrocardiogram signal.

2. Apparatus according to claim 1, wherein a plurality of the biometric sensors are arranged in an array distributed across the body support.

3. Apparatus according to claim 1, comprising a bed that includes the body support, and the biometric sensors are arranged fixed in the bed.

4. Apparatus according to claim 3, wherein the biometric sensors are arranged on an upper sleeping surface of the bed.

5. Apparatus according to claim 1 wherein the processing means is arranged to capture a plurality of electrocardiogram signals measured from a respective plurality of the biometric sensors and to determine the body position from the plurality of electrocardiogram signals.

6. Apparatus according to claim 1 wherein the processing means is adapted to compare the QRS complex of the at least one electrocardiogram signal with a plurality of prerecorded electrocardiogram signals in respective body positions and to identify a closest match.

7. Apparatus according to claim 1 wherein the biometric sensors are capacitive electrodes.

8. Apparatus according to claim 1 wherein the biometric sensors are contact electrodes, the apparatus further comprising a conductive foot contact and/or conductive pillow on an upper surface of the body support to serve as a return path for electrical current.

9. A method of measuring body position, comprising:
    supporting a body on a body support having electrocardiogram sensors fixed with respect to the body support;
    capturing at least one electrocardiogram signal from respective electrocardiogram sensors, the at least one electrocardiogram signal changing with body position as a result of variation of electrocardiogram potential over the surface of the body; and
    determining the body position from the at least one electrocardiogram signal using the variation of electrocardiogram potential over the surface of the body;
    wherein the determining of the body position from the at least one electrocardiogram signal includes:
        determining a polarity of the QRS complex of the at least one electrocardiogram signal, and
        determining an angle between an electrical axis of a heart of the body and an orientation of a respective pair of the electrocardiogram sensors from the polarity of the QRS complex.

10. A method according to claim 9, wherein the determining of the body position from the at least one electrocardiogram signal includes comparing the QRS complex of each electrocardiogram signal with a plurality of prerecorded electrocardiogram signals in respective body positions and identifies the closest match.

11. A method according to claim 9 wherein the electrocardiogram sensors are arranged as an array over the surface of a bed and the measuring of body position includes determining which electrocardiogram sensors of the array can detect the at least one electrocardiogram signal and measuring the body position from the at least one electrocardiogram signals from the determined electrocardiogram sensors.

12. The method of claim 9, wherein the electrocardiogram sensors include a conductive textile electrode array integrated in a bed sheet.

13. The method of claim 12, wherein the sheet includes a foot region of conductive textile that serves as a ground plate.

14. The method of claim 12, wherein a conductive pillow provides a return path for electric current.

15. A non-transitory computer readable medium that includes a program that, when executed by a processor, causes the processor to:

receive signals from at least two biometric sensors arranged in a fixed position with respect to a body support, the biometric sensors providing at least one electrocardiogram signal from a body, wherein the at least one electrocardiogram signal changes with body position as a result of the variation of electrocardiogram potential over the surface of the body; and determine the body position from the received signals using the variation of electrocardiogram potential over the surface of the body;

wherein the processor determines the polarity of a QRS complex of the at least one electrocardiogram signal to determine the orientation of the heart with respect to the respective pair of the biometric sensors providing the at least one electrocardiogram signal.

16. The medium of claim 15, wherein the program causes the processor to compare the QRS complex of the at least one electrocardiogram signal with a plurality of prerecorded electrocardiogram signals in respective body positions and to identify a closest match.

* * * * *